US00PP14208P29

(12) United States Plant Patent
Hofmann

(10) Patent No.: US PP14,208 P2
(45) Date of Patent: Oct. 7, 2003

(54) GERANIUM PLANT NAMED 'PACBLUSY'

(50) Latin Name: *Pelargonium×peltatum*
Varietal Denomination: 'Pacblusy'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/292,319

(22) Filed: Nov. 12, 2002

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Webb Ziesenheim Logsdon Orkin & Hanson P.C.

(57) ABSTRACT

A new and distinct ivy geranium plant with bluish-pink colored flowers above medium green foliage.

2 Drawing Sheets

Botanical classification: *Pelargonium×peltatum* (ivy geranium).
Varietal denomination: 'Pacblusy'.

BACKGROUND OF THE INVENTION

The present invention comprises a new and distinct cultivar of geranium known by the varietal name 'Pacblusy'. The new variety was discovered as a seedling in a selective breeding program in Dresden, Germany. The new variety is the result of a combination breeding of unnamed, unpatented selections from breeding group 8K-48. Plants of the new variety exhibit similar flower color of their parents, but produce double flowers. The new variety was first asexually reproduced by cuttings in Dresden, Germany in 1999. The new variety has been trial and field tested and has been found to retain its distinctive characteristics and remain true to type through successive propagations.

DESCRIPTION OF THE DRAWING

The accompanying photographic drawings illustrate the new variety, with the color being as nearly true as is possible with color illustrations of this type.

DESCRIPTION OF THE PLANT

Figure 1:
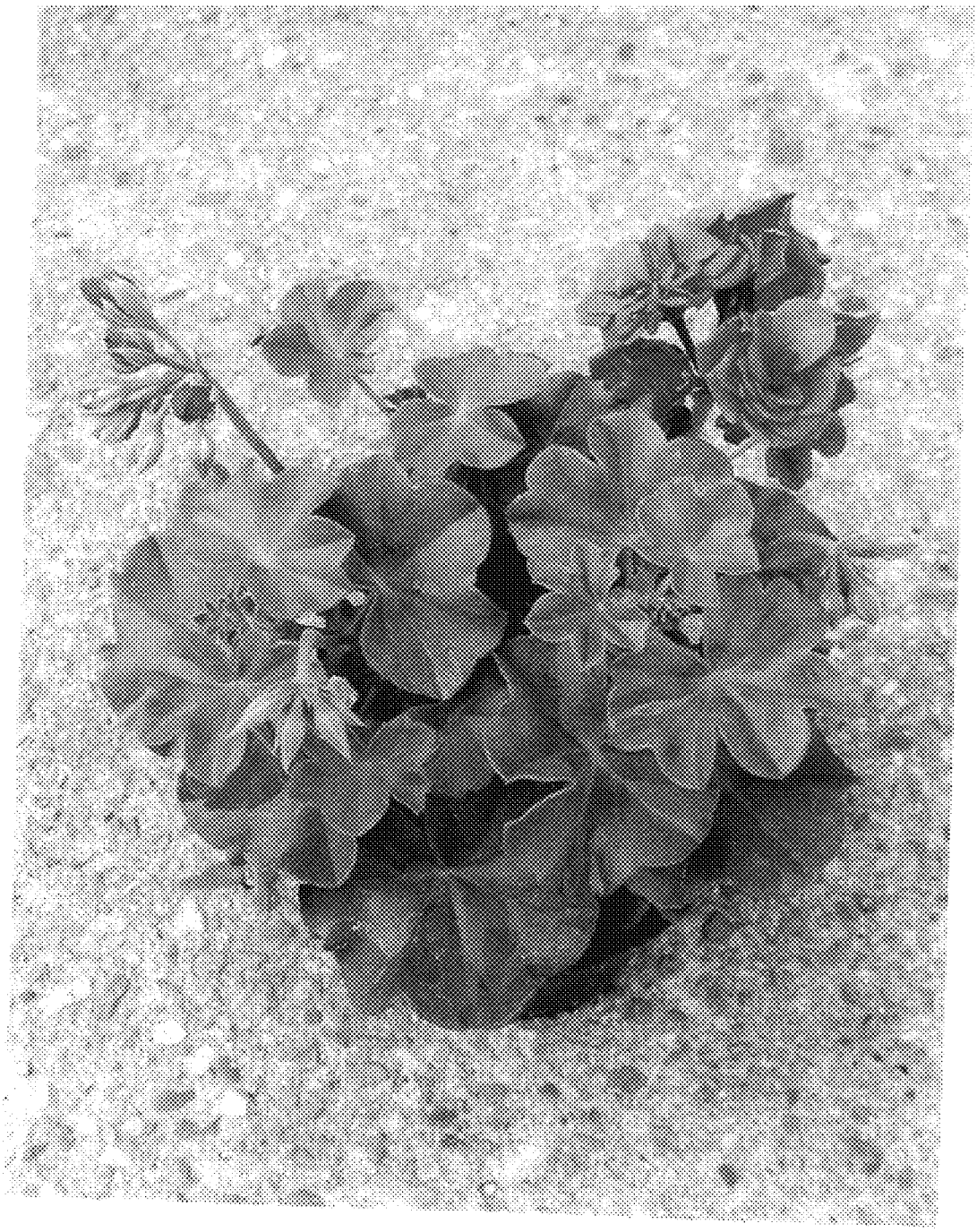
FIG. 1 is a photograph of the plant.
Figure 2:
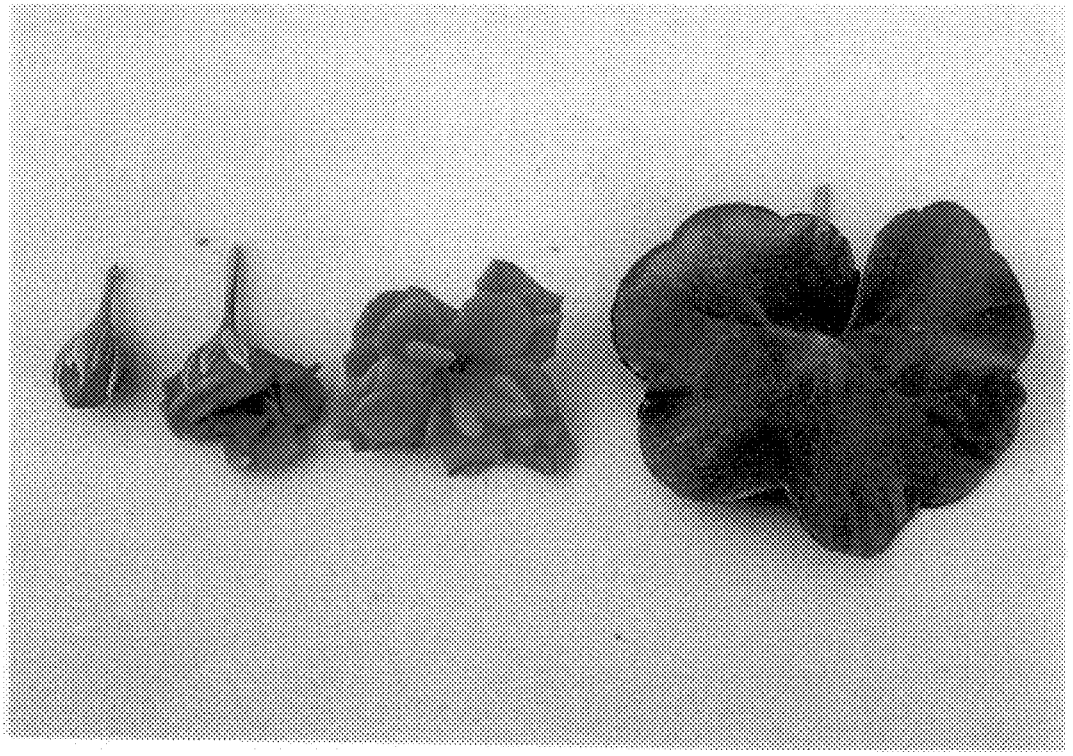
FIG. 2 is a photograph of a bud just showing color, a bud beginning to open, a flower, and a leaf.

The following detailed description sets forth the characteristics of the new cultivar. The data which defines these characteristics were collected from plants propagated in January, potted in February, and grown in a greenhouse and then outdoors in June for data collection in Dresden, Germany. Plants were 9 months old when described. The color readings were taken on a plant under natural indoor light. Color references are primarily to The R.H.S. Colour Chart of The Royal Horticultural Society of London.

PLANT

Height: About 11 cm from media surface to top of foliage; about 15 cm from media surface to top of umbels.
Strength: Does not require artificial support.
Growth: Cascading, well-branched.

Roots: White; adventive; 3.5–4 weeks to develop.
Leaves:
- *Arrangement.*—Opposite middle zonation.
- *Size.*—Length: 3.4–3.8 cm. Width: 5.5–6.5 cm.
- *Shape.*—Overall: Reniform. Base: Open. Apex: Pointed.
- *Margin.*—Entire with lobes.
- *Pubescence.*—Very few hairs.
- *Color.*—Upper surface: 137B. Lower surface: 143A. Zonation: Darker than 137B.
- *Ribs and veins.*—Venation: Net-like. Color: 141C on lower surface.

Petioles:
- *Color.*—141C.
- *Length.*—3–4 cm.

Stem:
- *Color.*—141C.
- *Overall stem length.*—15–17 cm.
- *Internode length.*—1.5–3.5 cm.
- *Lateral branch length.*—About 16 cm.

THE BUD

Shape when closed:
- *Overall.*—Spherical.
- *Individual bud.*—Elliptical.

Size when closed: 5–6 cm across cluster.
Bud size: 1.4 cm in length, 0.8 cm in diameter.
Color: 74B.

INFLORESCENCE

Size of umbel:
- *Width.*—About 8 cm.
- *Length.*—4–5 cm.
- *Depth.*—4–5 cm.

Borne: Umbel; Flower on pedicel, pedicel on peduncle.
Flowers:
- *Form.*—Zygomorph.
- *Number of flowers per umbel.*—5–8.
- *Size.*—Diameter: About 5 cm. Depth: About 1.5 cm.

Petals:
- *Color.*—Upper surface: 74B. Lower surface: 74A. Shape: Overall: Round to oval. Base: Pointed. Apex: Rounded.
- *Size.*—2.0–3.0 cm long, 1.5–1.8 cm wide.

*Margin.*—Entire.
*Number per flower.*—25–30.
*Texture.*—Smooth.

Sepals:
*Color.*—Upper surface: 143B. Lower surface: 143B.
*Shape.*—Overall: Narrow, pointed. Apex: Narrow, pointed. Base: Wider than apex, not pointed.
*Size.*—Length: 1.2–1.4 cm. Width: 0.2–0.3 cm.

Petaloids:
*Quantity.*—0–3 per flower.
*Shape.*—Irregular.
*Color.*—74B upper surface, 74A lower surface.

Pedicel:
*Length.*—2.2–2.4 cm.
*Color.*—Ranges between 166A and 143B.

Peduncle:
*Length.*—7–8 cm.
*Color.*—143B.

Lastingness of umbel: About 3 weeks.

Natural flowering season: Early flowering; blooms continuously through summer; plant lasts until frost.

Disease/pest resistance: No susceptibility to diseases or pests has been noted to date.

REPRODUCTIVE ORGANS

Stamens: Absent.

Pistils:
*Number.*—One.
*Length.*—0.1 cm.
*Stigma.*—Pink.
*Style.*—Length: 0.6–0.7 cm. Color: 142D.
*Ovaries.*—Superior, pubescent, about 0.1 cm long, 142C.

Seeds: Rarely present; if present, 5 per flower, 0.4 cm long, colored 165A.

GENERAL CHARACTERISTICS

1. Doubled flowering with rosebud appearance.
2. Short internodes.
3. Tetraploid.
4. Good rooting.
5. High yield of cuttings.

I claim:

1. A new and distinct variety of geranium plant substantially as shown and described.

* * * * *